United States Patent [19]

Espinoza et al.

[11] Patent Number: 5,807,232

[45] Date of Patent: Sep. 15, 1998

[54] PROCESS FOR THE TREATMENT OF SACCHARIDE THREE DIMENSIONAL STRUCTURES FOR THE REACTIVATION OF RECOGNITION MECHANISMS AMONG ANTIGENS AND ANTIBODIES

[76] Inventors: Fausto Leal Espinoza; Alberto Cornejo Lizarralde; Jose Manuel Flores Hernandez; Victor Vargas Varela, all of Blvd. Touca No. 13, Letra E. Naucalpan C.P. 53100, Mexico

[21] Appl. No.: 713,272

[22] Filed: Sep. 12, 1996

Related U.S. Application Data

[63] Continuation-in-part of Ser. No. 322,493, Oct. 14, 1994, abandoned.

ROTATION EFFECT

ISOMERS

RESONANT EFFECT

MAGNETIC FIELD
POSITIVE SEQUENCE

FIG.8B

ROTATION EFFECT

ISOMERS

RESONANT EFFECT

MAGNETIC FIELD
NEGATIVE SEQUENCE

POSITIVE SEQUENCE

FIG.10B

NEGATIVE SEQUENCE

PROCESS FOR THE TREATMENT OF SACCHARIDE THREE DIMENSIONAL STRUCTURES FOR THE REACTIVATION OF RECOGNITION MECHANISMS AMONG ANTIGENS AND ANTIBODIES

CROSS REFERENCE TO RELATED APPLICATION

This application is a continuation-in-part of U.S. application Ser. No. 08/322,493 filed Oct. 14, 1994 now abandoned.

BACKGROUND OF THE INVENTION

Field of the Invention

The present invention relates to a process for the stereochemical modification of three dimensional structures of saccharides by the use of electromagnetic energy, and more particularly to a method of reactivation of cellular and molecular pattern recognition mechanisms among antigens and antibodies as well as to the somatic molecular recognition action through the use of isomeric shifts induced in the three dimensional structures of saccharides by means of electromagnetic energy in the visible light range.

Recent studies have shown the great interrelation between sugars and normal as well as pathological processes in living beings.

It is known in fact that the carbohydrate moiety of infectious agents plays a very important part in the recognition or non-recognition process of antigens.

It is through these sugars that the method of the present invention acts on the viral and/or bacterial infectious processes.

Viral infections have acquired extraordinary relevance since the development of the human inmunodeficiency virus (HIV) producing the acquired inmunodeficiency syndrome (AIDS).

When an infection arises, the agents that cause the infection arrive at specific sites on the cellular surfaces which are known as receptors. Antibodies can recognize the agents by their molecular three dimensional topology (structure).

The arrival of the infective agents to their receptors with their specific molecular topology requires that the macromolecules of the agent and the receptor assemble in an exactly complementary manner, forming a coupling called "lock-key". All macromolecules being assembled to form the complementary respective pair are three dimensional structures.

All three dimensional molecules of the receptors located on the cell surface are present in a large variety of structures amounting to millions and each one is specific for a particular cellular recognition .

However, there are infections that have the capacity to overcome this great variety of receptors which form the recognition mechanisms and that have as well the capacity to produce three dimensional molecular figures in larger quantities than the figures that comprise the cellular recognition mechanisms.

Saccharides are present on the infective agents and they are located in the macromolecules that intervene in all infections, such as glycoproteins, lectins and endotoxins.

Due to the fact that all saccharides are structures with asymetric carbons and that they have the potential for stereoisomers at each asymetric carbon, they present a very large range of possible natural three dimensional structures.

All three dimensional macromolecules of the complementary pairs of any assembly or infection depend to a great extent on oligosaccharides and polysaccharides contained in glycoproteins, lectins and endotoxins involved in the infection.

Consequently a constant has been discovered, it is involved in all infections and comprises two aspects:

First, sugars are capable of forming the complementary pairs because they contain enough enantiomeric structures to form each one of the required complementary pair and still be sugars, no more and no less than the optical isomers recognizable by the immune system both in the innate phase as well as in the adaptive phases.

Therefore all saccharides have the capacity to assemble in oligosaccharides and polysaccharides and thus have the possibility to have an enormous amount of isomers in numbers amounting to millions and thousands of millions.

Second, since the haptens are the nonprotein portions of an antigen being responsible for its specificity for the antibodies, it has been discovered that sugars are the only members of the determining proteins in the virus membrane, that is, the only haptens capable of modifying the molecular topological figures to form millions of complimentary pairs of infectious assemblies because they are on the surface of natural molecules, presenting an infinite capacity of three dimensional or conformational changes due to their high isomerism.

BACKGROUND OF THE INVENTION

As to the best knowledge of applicants, there is up to this date no method for the alteration of saccharides allowing this production of multiple macromolecules with the goal of reactivating the recognition mechanisms among antigens and antibodies.

There is also no method that uses electromagnetic energy in the visible light range to achieve the above-mentioned objective.

All research carried out to face the problems provoked by viral infections or tumoral developments, has been focussed on the discovery of active ingredients with antiviral or antitumoral characteristics to be provided by any administration route suitable for patients suffering such conditions.

These investigations have not been as successful as desired, particularly regarding infections by HIV. In addition, the side effects of many therapeutic agents have been much too severe even using recently discovered procedures directing the active ingredients specifically to the site of the infection.

In this fashion U.S. Pat. No. 4,320,141 to Komatsu et al. describes a method for the treatment of tumors in patients which comprises administration thereto of an antitumoral composition containing an active ingredient. In contrast, the present invention is not aimed at the production of an active ingredient, but to the modification of the orientation of the molecular structure of the saccharides involved in the infection.

U.S. Pat. No. 4,749,716 to Funaki et al., refers to one of two geometrical isomers of a triazole active compound to be used as a fungicide, herbicide and/or planar development regulator in agriculture and horticulture. Even when an isomerization process is mentioned it is not directed to the saccharides involved in a viral infection process and it is not destined to the use intended by the present invention.

U.S. Pat. No. 4,471,640 to Levitt et. al., mentions in the description that alkene photoisomerization is known in the literature and through which cis and trans isomeric mixtures can be made and that cis isomers can be isolated by means of crystallization, distillation or chromatography in a step appropriate in the synthetic sequence. Though, photoisomerizationis known in the case of the above referred patent, this is done to obtain a product with herbicidal characteristics and the use is not directed to saccharides and does not have the same object that the present invention has.

U.S. Pat. No. 4,680,053 to Levitt et al., references U.S. Pat. No. 4,461,640 and the comments stated above are also valid in this case.

SUMMARY OF THE INVENTION

It is the objective of the present invention to provide a unique method which gives sufficient elements, with the necessary mechanisms, for the production of three dimensional macromolecules with somatic and virus variations, including genetic, intervening in the isomerization of the involved saccharides.

Another object of the present invention is to provide a unique method, allowing intervention in the mechanisms of the sugar mediating in viral infections, identifying those liable of modification, in order to be able to control, stop and eliminate them.

Still another object of the present invention is to provide a unique method in which the production of the multiple saccharide macromolecules is reached through the use of electromagnetic energy in the visible light range.

An advantage of the unique method of the present invention is that by orienting the very different forms of sacharide geometric figures, the method allows the effective recognition of antigens and antibodies.

Still another advantage of the unique method of the present invention is that by treatment with a non-invasive method, the undesirable side effects are eliminated. The whole body of the patient is treated in the method of the invention, not only the afflicted zone.

"Unique method" in the present description means a method unifying the reactivation mechansims of the cellular and molecular recognitions between antigens and antibodies as well as the somatic molecular recognition.

"Unique method" means also the method applied to the combined and simultaneous electromagnetic energy range, with correlative values to obtain the individualized isomers required in each case.

The objects and advantages previously pointed out will be evident and other will become evident when proceeding with the description of the invention with reference to the drawings and the following examples.

BRIEF DESCRIPTION OF THE DRAWINGS

Diagonal lines represent the fall speed in the CD4 count which when crossing the abscissas in tx pass to dead zones (M) when no application of the method of the present invention exists.

On the other side, horizontal dotted lines originating in 20, 50 and 210 CD4s, represent cases treated with the present unique method, which have already exceeded the terminal phase survival of HIV infection by five or more times=5 (tx).

DESCRIPTION OF THE INVENTION

A process for the alteration of saccharides with electromagnetic energy in the visible light range to reestablish pattern recognition mechanisms among antigens and antibodies of the present invention, comprising the following steps:

a) obtaining the analytic guidelines for determining the necessary parameters to optimize the procedure.

b) correlating the infection mechanisms with the recognition mechansims and, c) Subjecting the saccharides involved in the viral infection to electromagnetic energy.

Figure 8A:
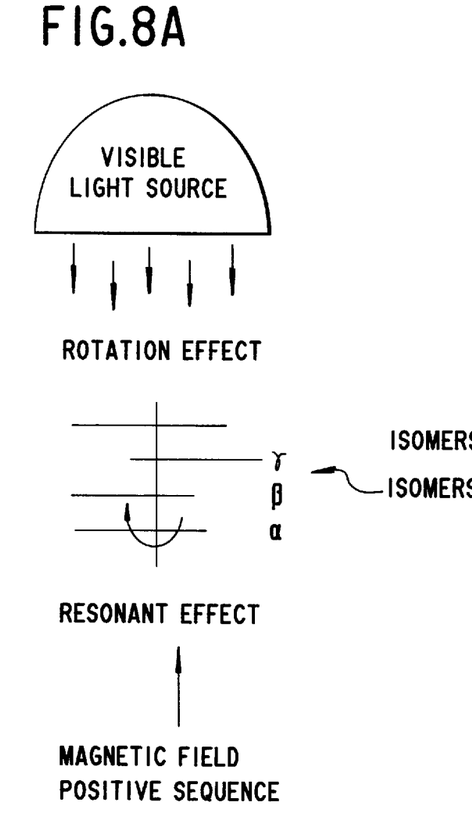
FIG. 8 shows how energies are combined to obtain the desired rotation.
Figure 8B:
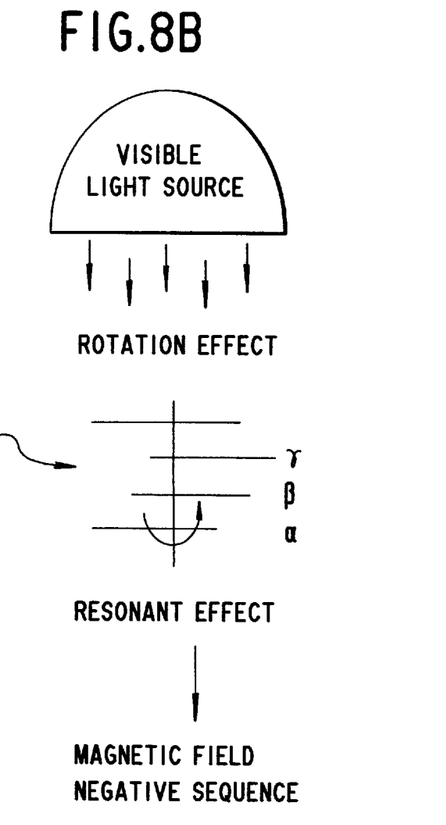

Once the patient's blood pH has been determined, and the type of antigen (viral, bacterial or somatic) has also been determined; as well as an assymetrical carbon that results from the analysis (it could be alpha, beta or gamma type, see FIG. 8), the induction procedure is chosen in relation to a positive or negative sequence of phases, strength of magnetic field and kilocal/mol of photonic energy. The diagnosis is obtained from standard laboratory tests or referring physicians.

Once the type of antigen and its receptor is known, the correlation algorithm will provide the calculated rotating value for each saccharide. The relation between kilo-cal/mol and the degree of shift (rotation) from one carbon to another is well known by those skilled in the art, therefore knowing the natural degree of rotation of a molecule (angle) the algorithms calculate the kilo-cal/mol needed to shift the molecule to the closest idosa configuration (next angle), this approach could be clockwise or counter clockwise which means a positive or negative sequence of the magnetic field. For details on the relationship between Kcal/mol and rotation angles, the following references may be consulted: Organic Chemistry, Stephen J. Weininger, Worcester Polytechnic Institute, p.87 (1969); Organic Chemistry, Loise F. Feiser and Mary Feiser, Chemistry Department, Harvard University, Reinhold Publishing Corporation, New York, p. 355 (1956); or General Chemistry, Babor-Ibarz, 4th Edition, p.780.

Patients with specific diagnoses may be treated according to the following guidelines. Blue light of wavelength 3800 to 4920 Angstroms is used to treat patients with brain diseases. Green light of wavelength 4920 to 5770 Angstroms is used to treat patients with HIV Yellow light of wavelength 5770 to 5970 Angstroms is used to treat patients with various cancers. Red light of wavelength 5970 to 7800 Angstroms is used to treat patients with diabetes. For all patients ev of 1.6 to 3.2 is used.

Patients may be treated with the range indicated above for a different type of condition, or with the entire range of light in the visible light range.

This correlation means in other words the searching and finding of a key to every lock or an antibody to any antigen. With this principle, the immunological system identifies the antigen (that was not identified before) because after the rotation of the saccharide produced by the electromagnetic energy, it can recognize the three dimensional figure that the immunologic system is familiar with.

It has been proven in laboratory tests that the electromagnetic energy needed is a strength field varying between 100 and 1000 Gauss, and it has been observed also that the preferred strength range varies between 300 and 600 Gauss, and that it should be produced with a sequence of negative and positive phases, combined and simultaneous with photonic electromagnetic energy with a wavelength varying between 3000 and 7000 Å and preferably in the scale varying between 4000 and 6000 Å. The method of the present invention uses light of the wavelength in the visible range. The light may be or not be concentrated, and from only a narrow range, or from a larger spectrum.

The electromagnetic energy of this method will operate in the frequencies range of 5 Hz to 50kHz, with the preferred range from 50 Hz to 5 kHz, while the photonic electromagnetic energy operating frequencies vary within the range of 400 terahertz to 800 terahertz as an operating range and a preferred range from 500 to 660 terahertz, coherent or not.

The photonic electromagnetic energy power varying within the range of 1 ½ electron volts to 3 ½ electron volts, polarized or not polarized and availability of 3 to 3000 kilocalories per mole photons.

The objective of the photonic energy is to isomerize the monosaccharides, oligosaccharides and polysaccharides on the outside surface of biological cells. The electron-volts equivalent to the kilo-cal/mol ratio of photons required to produce stereochemical movement with the aim to isomerize is used. This rotation activity is made based on the energy conservation law as an optical reaction known as a photochemical reaction.

The radiation sources are polarized or non polarized industrial light bulbs which emit light in the visible spectrum. See FIG. 9.

In laboratory tests the selection of light source is determined based on the technical specification data like wavelength energy distribution and the amount of energy at the proper frequency for the precise desired rotation (patient's needs). As noted above, there are preferred wavelengths for different conditions, but there have also been instances where a patient responded best to a wavelength selected for another condition, or to a broader range of the visible light range. Thus, the above preferred ranges represent only a starting point for the choice of wavelength.

The generation of two different sources of energy, in Gauss/Hertz and electron-volts/terahertz, is obtained by individual and independent devices (magnetic three phase coil and light bulbs).

The statement of leaving one constant or not and another pulsant or not, means:

a) Either the magnetic energy or the photonic energy could be applied to the patient (for example, only the photonic energy) or combined (both energies together), this is selected by the rotation necessities, or keeping one energy fixed and the other variable.

b) The magnetic energy or the photonic energy could be applied in a steady form (continuous emission) or pulsating (periods of time when emission is present or not).

Once the characteristics of the electromagnetic energy used in the present method have been established, reference is made to the frequency and exposure time of the saccharides to reach the modification of the three dimensional structures.

The exposure of the saccharides to the energy of this method is given in a range variation between one exposure per day to one per month and with exposure times varying between 5 and 50 min. per exposure, for a blood pH between 7 and 8.

The aim of the application of magnetic energy (to resonant cell) and photonic energy in the visible spectrum (to rotate cell) is a biophysical reaction which activates the pattern recognition cellular mechanism enzymatic type, it is the search of the complementary lock (antigen) and key (antibody) via saccharides that work as an intermediary function to cover the difference between antigens and antibodies. This almost unlimited intermediation function is due to the isomeric action of saccharides.

In order to obtain these biophysical results the accomplishment of a field strength from the magnetic coil (Gauss) and the electron-volts equivalent to the kilo-cal/mol of photons needed to rotate the cells (photonic energy in the visible light) are applied to the patient in the exact and precise amount of combined energies to obtain the desired rotation (antigen-antibody identification). See FIG. 8.

The amount of kilo-cal/mol that are necessary to rotate a molecule is well known by those skilled in the art, therefore choosing the proper frequency and energy (ev), the molecule rotates to find a recognized three dimensional structure that the immunologic system identifies.

Figure 10A:
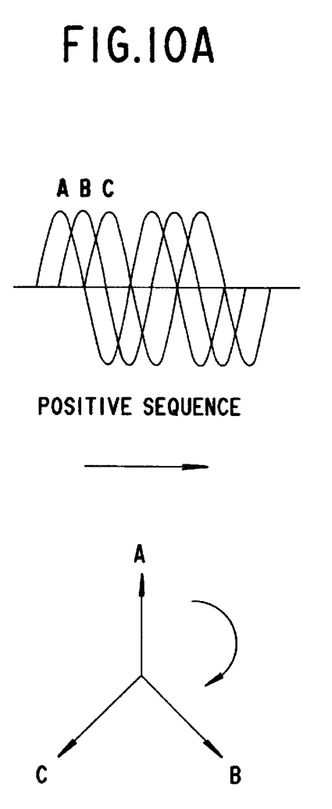
FIG. 10 shows the sequence of phase arrangement.
Figure 10B:
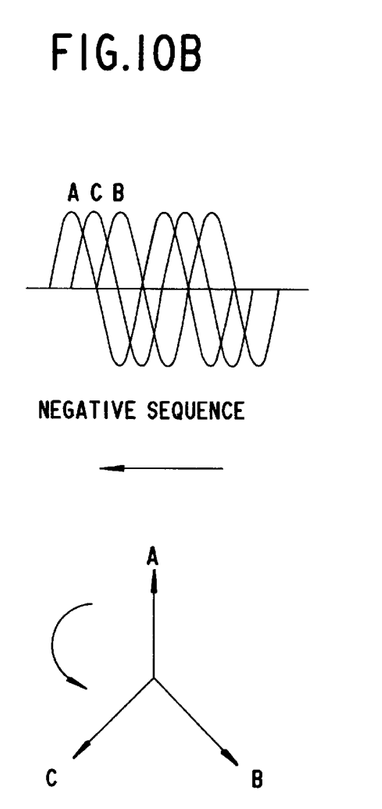

The objective of the magnetic field is to induce in the monosaccharides, oligosaccharides, and polysaccharides on the outside surface of biological cells the magnetic resonant effect via a continuous and overlapping three phase magnetic field. The molecular rotation of cell motion clockwise or counter clockwise is obtained by choosing the proper sequence of phases in the three phase magnetic field, (see FIG. 10) if the magnetic field system inverts two terminals, a different field sequence is obtained, similar to the procedure of changing rotation in an induction motor.

According to the technical specification data the magnetic field strength is obtained with only one pole and three winding circuits, each one for each phase, the strength of the field is obtained with the variation of induction current for each circuit.

Figure 9:
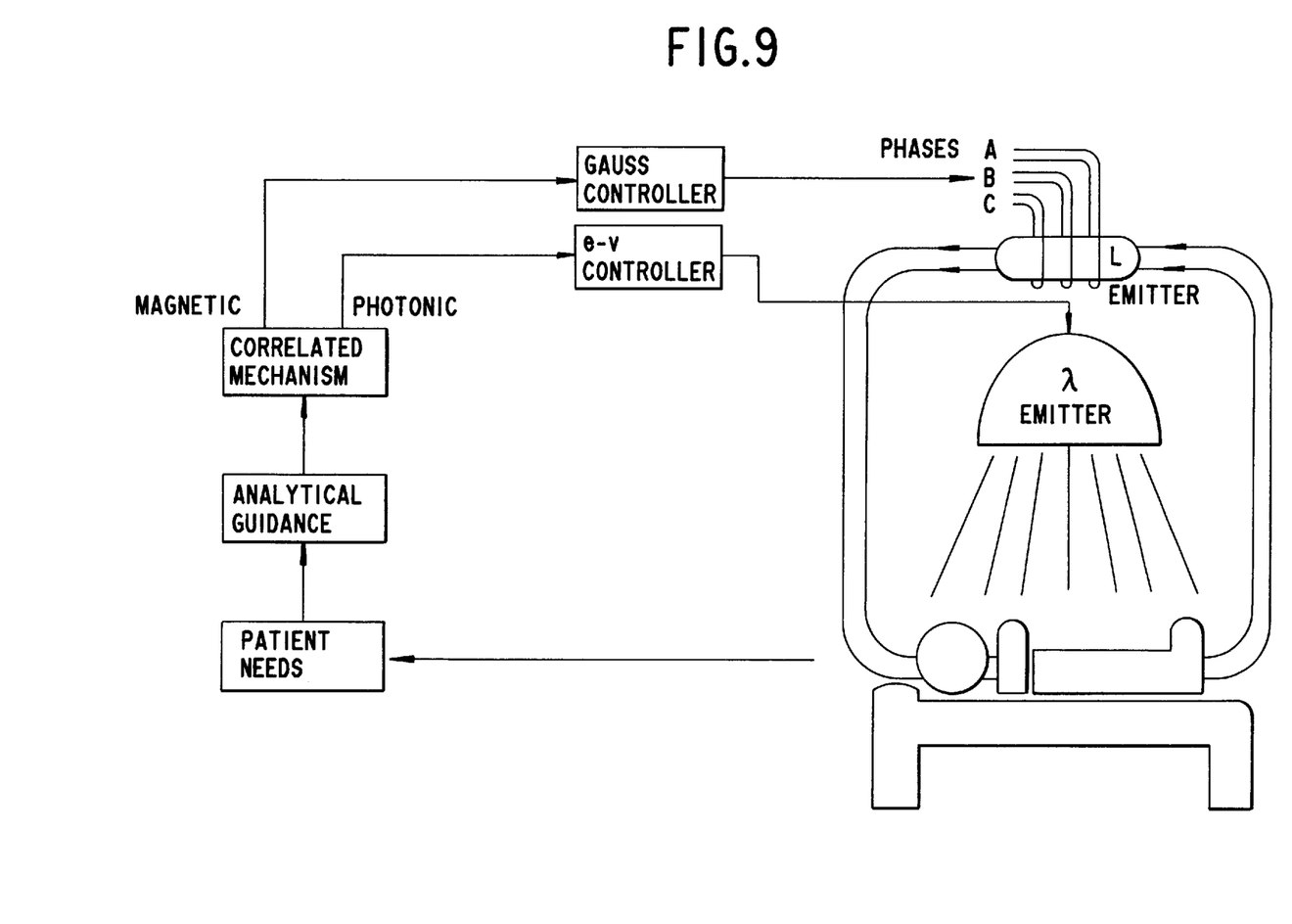
FIG. 9 shows the method and apparatus for the method of the present invention.

In FIG. 9 the magnetic induction arrangement is shown, including sequence of phases application and how a patient is treated.

Particular and preferred embodiments of the invention have been shown and illustrated and it is evident that those skilled in the art can make several changes and modifications without departing from the spirit and scope of the present invention, thus it is intended that the above description be considered in an illustrative and non-limiting sense and that the scope of the invention be only defined in the terms of the following claims.

EXAMPLES

Examples 1–7 represent individual examples. Examples 8–11 show summaries of many patients treated according to the present invention.

Of the following seven examples the first three refer to 3 patients suffering from human immunodeficiency virus (HIV), example 4 refers to uterine cavity excreting insufficiency, example 5 is related to the effect on the ocular cavity and examples 6 and 7 refer to prostate cancer and bone marrow cancer respectively.

Example 1

Female patient, adult, infected with the human immunodeficiency virus, was prepared with broad energy spectrum each time with an application of 0.5 hours, the patient's evolution is given by several laboratory tests carried out on the dates mentioned.

| LABOR- | DATE | | | | |
|---|---|---|---|---|---|
| ATORY | 2/2/91 | 23/1/91 | 13/2/92 | 3/31/92 | 12/4/92 |
| GR | — | — | 3,100,K | 3,950,K | 4,010,K |
| Hb | — | 11.3 | 9.6 | 12.3 | 12.1 |
| Hcto | — | 34 | 28 | 37 | 37 |
| GB | — | 5,500 | 2,300 | 9,050 | 5,100 |
| N | — | 48 | 40 | 50 | 52 |
| Lc | — | 51 | 55 | 43 | 45 |
| Mn | — | 0 | 03 | 0 | 2 |
| Eo | — | 0 | 05 | 07 | 01 |
| HIV | + | — | 1,450 | + | — |
| CD4 | — | — | — | 210 | — |
| CD8 | — | — | — | 690 | — |
| AGP24 | — | — | — | — | POSITIVE Sample taken in II-13 to prove there is HIV "outside" the battle field. |
| REMARKS: | — | 1 | 2 | 3 | 4 |

1) Evident retroauricular ganglions, palpable, firm 2–3 cms. loose feces, some depression, no fever.
2) Reduction in the size of the ganglions.
3) No variation in the ganglion's size, hard consistency of feces, and reports weight increase, shows a better mood, ratio CD4/CD8's, 210/690=0.30
4) During this period the patient reports feeling the ailments of a cold, 2 days evolution fever is not thermotreated, patient even said it disappeared, ganglions evidence increase in size although not in number, firm no pain, refers also to myalgias. Reports no loss of appetite, perspiration or alteration in the consistency of the feces. Makes no reference to other alterations.
5) Patient is evaluated after three weeks, reports feeling better the above mentioned scheme disappeared. Ganglions have again reduced their size.

Figure 1:
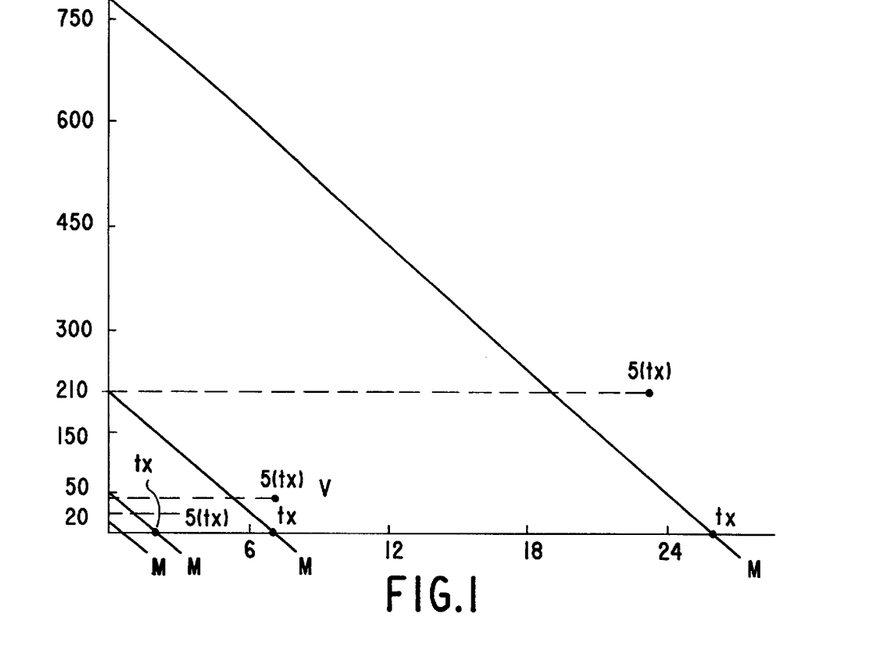
FIG. 1 is a graph showing the reestablishment of the immunologic system in positive cases of HIV infection, and wherein the ordinates represent the CD4 proteins obtained by analysis the previous week to the start of the application of the unique method of the present invention, and the abscissas represent time in a scale of months.
Figure 2:
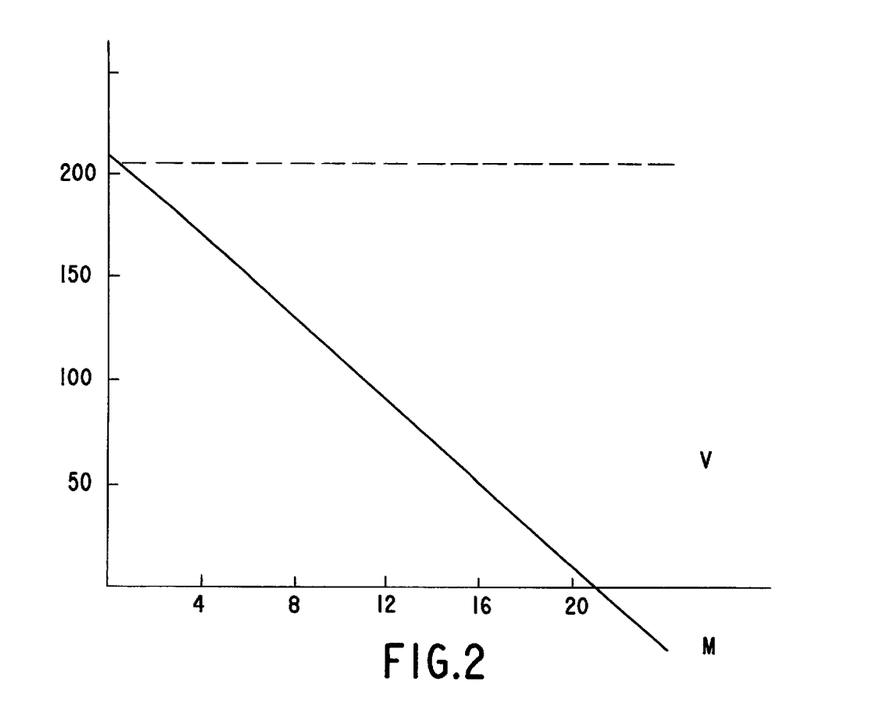
FIG. 2 is a graph representing the same as FIG. 1 but with the difference that it is only directed to the case of example 1 and wherein the abscissas represent weeks.

It should be noted that:
1. Given the results of the analysis in March 1992, only 210 reported in CD4, life expectancy was of 2 or 3 months at the most but by November 1993 patient is still alive. (FIG. 2).
2. On November 1993 a good health state is reported, breaking the records of AZT of worldwide use, with a magnificent survival time, but above all with a much better quality of life.
3. Results of monthly hemograms, accompanying the events given during the months of application of this method wherein are evident the stages of:

| FALL | RECOVERY | TURN | REESTABLISHMENT |
|---|---|---|---| in white cells with the antibodies.

Cellular movements testify that there has been an immunologic reactivation with the typical response of an automatic control not only implying the shape of the graph but the coincidence in time of reactivation with only 210 CD4's.

Example 2

Adult patient infected with the human immunodificiency virus, was treated for a term of three months, twice a week, half an hour each time.

Following results of the real analysis given in the cited dates are given.

Example 2

Adult patient infected with human immunodeficiency virus, was treated for a term of 3 months, treatment of 2 times a week, being half an hour each one.

Following are given the results of the real analysis given in the cited dates.

| 1993 | W. Blot | ELISA | Erit. | Leuc. | CD4 |
|---|---|---|---|---|---|
| April | | (−) | | | |
| July 13 | | | 4,640 K | 9,000 | |
| July 30 | | (+) | | | |
| July 30 | | | 2,950 K | 6,000 | |
| September 10 | | | 3,830 K | 10,000 | |
| September 20 | | (+) | | | |
| October 14 | | | | | |

Taking into account the symptoms of the case and the results previously established and considering that the analysis by ELISA cannot give false negatives, there is an example of HIV evolving to unrecognizable stereochemical structure by the antibodies (negative zone).

It is noted also, that after the half an hour treatment each of the broad spectrum energy of this method, ELISA analysis provided a positive result (positive zone).

Figure 3:
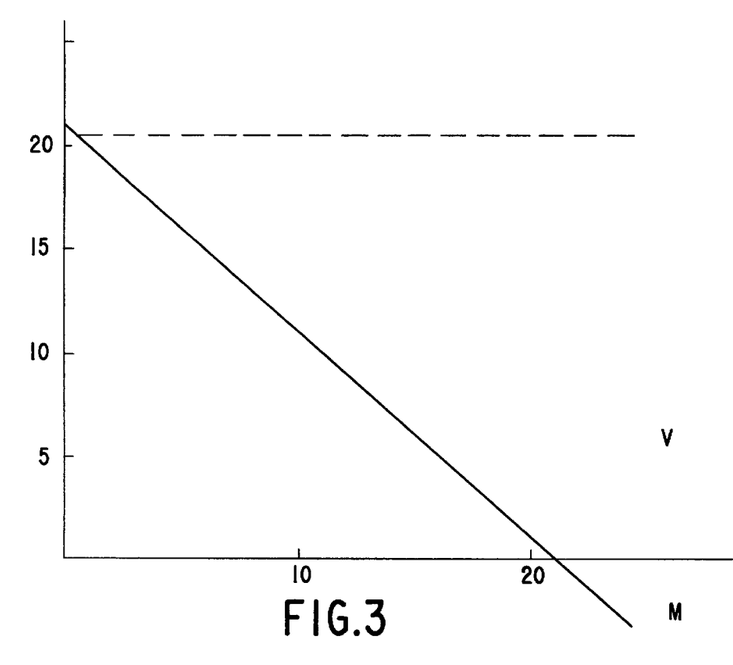
FIG. 3 is a graph representing the same as FIG. 1 but specifically directed to example 2 and with abscissas representing a scale of days.
Figure 4:
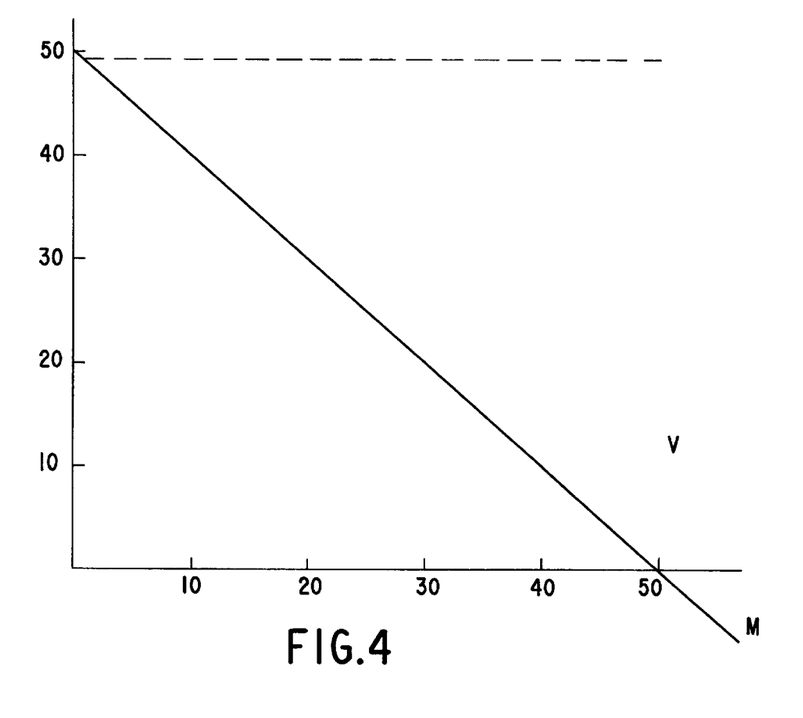
FIG. 4 is a graph representing the same as the previous graphs but specifically directed to example 3.
Figure 5:
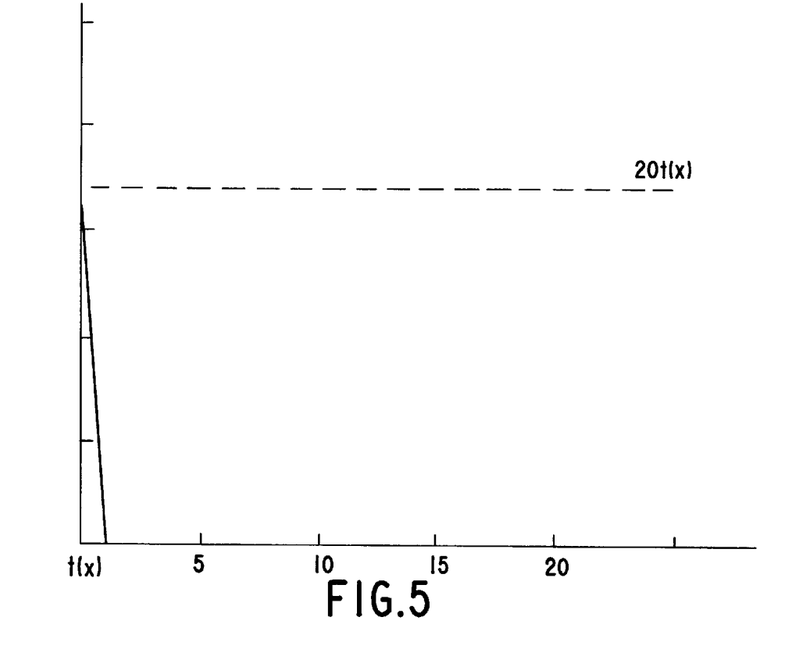
FIG. 5 is a graph illustrating the effects of method 1 of this invention in a juvenile diabetes case described in example 5, in which the improvement in eyesight of the treated subject is outlined, avoiding surgical intervention scheduled within two weeks (tx) and which has been postponed for more than two years=20(tx) with the advantage of a slight reduction of the insulin doses required in those two years.
Figure 6:
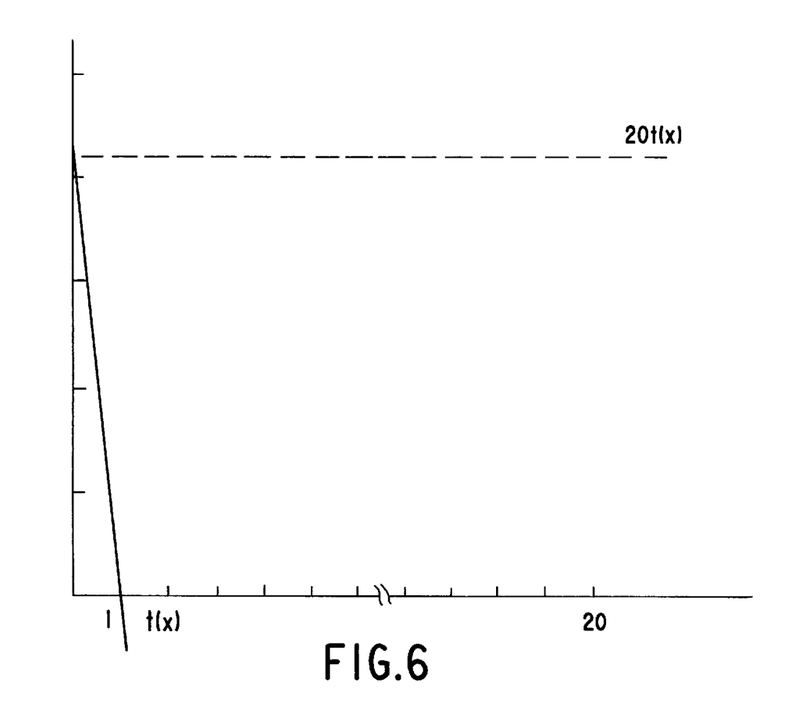
FIG. 6 is a graph specifically directed to example 6 in which the method of the present invention for a case of prostate cancer with metastasis is illustrated, the ordinates indicate the relative level of gravity, while the abscissas illustrate the expected time of survival (tx) without the use of the unique treatment of the present invention. The upper horizontal dotted line represents the survival of 20 times more=(tx) reached at the date with the use of the present method.
Figure 7:
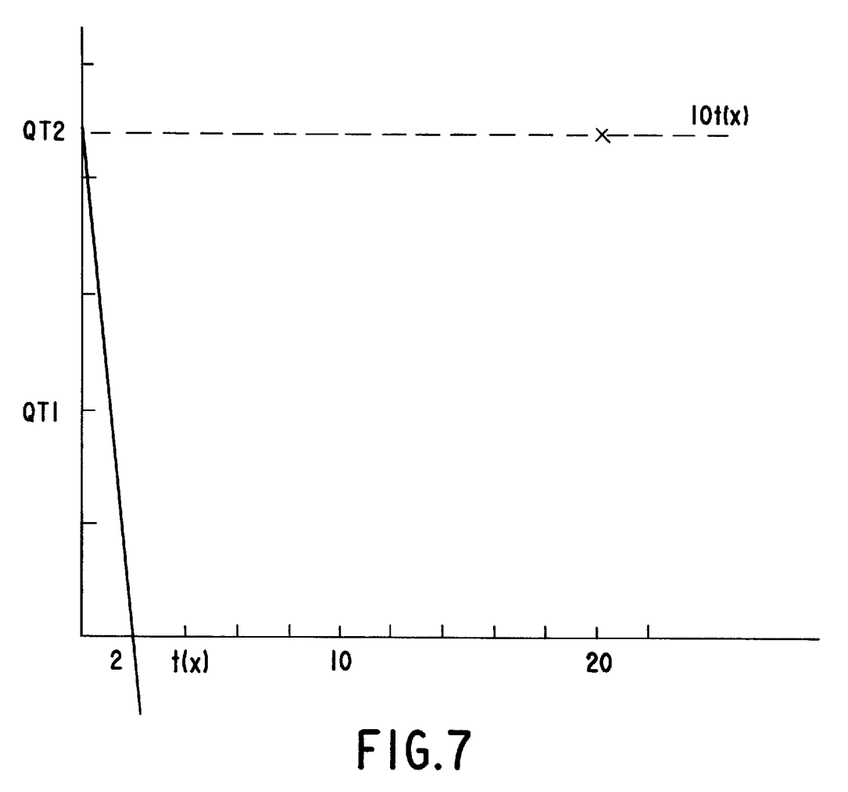
FIG. 7 is a graph specially designed to represent example 7, in which a bone marrow cancer case is treated with a relative gravity level and highlights the application of two chemotherapies represented in the ordinates as QT1 and QT2. The horizontal dotted line represents a survival reached at the period of 10 times =10 (tx) with the use of the present invention.

This is important as there are many cases in which analysis provides negative results, even when the patient is afflicted by HIV, upon existence of a real result imaginary pathologies diagnoses is avoided as well as the application of useless treatments and even with adverse results, allowing the CD4 count to keep falling which in this case was down to 14.7 cells instead of the normal 800 or 200 in seropositive symptomatic (FIG. 3).

The following stages can be noted from the results of the haemograms, after three months of treatment of the method of the present invention:

| FALL | RECOVERY | TURN |
| --- | --- | --- |

As a consequence of the above it should be noted that:

In the first state there was an HIV virus evolving to stereochemical figures unrecognizable to the immunological system.

In the second stage, there is a re-establishment in HIV to the original recognizable figures by the antibodies and an ELISA with positive results is obtained. To avoid the possibility of having a false positive, a Western Blot analysis is carried out to confirm; the result is a 100%.

In the third state the reactivation of the immunological system is shown which as in Example 1 counts with an automatic control of the infection occurring simultenously with only 14.9 CD4s (FIG. 3.)

Control of the infection is evidenced by the patient and consists of the disappearance of fevers, diarrhoea elimination, suspension of weight loss, and disappearance of pneumocytosis, tubercolosis, leucoplasias and lymphadenopathies.

Example 3

This example deals with a male patient with a resulting count of 59 CD4.

The response is the same as in example 1 and 2 and has been graphed in FIG. 3. The three examples have reached a life extension of over five times life expectancy (tx) than without this method and is marked as tx in graphs of FIGS. 1 to 4.

Example 4

Example 4 is related to results obtained in somatic cells when subject to the procedure of this method.

For this and the following example it is convenient to note that one of the twenty known sialic acids since the '80s with saccharide structure and its nine carbons is the main constiuent of the mucines excreted in the uterine and ocular cavities. In both zones its presence makes lubricant and its deficiencies cause severe effects.

A patient with uterine cavity excreting insufficiency was treated in the following manner:

Non-invasive and non-reactive energy from this method was applied 8 times, twice a week and exposure time was of 0.5 hours each. Patient was 8 months pregnant with prior caesarian section births and again scheduled for that procedure.

Reaching the scheduled date and after the above cited treatment the case turned from risky to normal and the birth proceeded without caesarean section, no complications prior to or after delivery.

Conclusion: Recovery was reached by altering the lubricating saccharide isomer and thus the location of the product and its exit route. Prior to the scheduled programmed anticipated release from the hospital due to rapid recovery.

Example 5

Adult male patient afflicted with juvenile diabetes was treated.

Exposure to broad energy spectrum was carried out twice a week, being the term of exposure of 0.5 hours each time, the following results were obtained:

After the first month of treatment the programmed eye operation was postponed.

During the second month of treatment the operation was cancelled.

Insulin dose is reduced in the third month as well as the lens graduation.

On the fourth month a reduction in the prescribed insulin is prescribed, a reduction in lens graduation was made too.

The insulin dose is again reduced during the fifth month as well as a reduction in lens graduation. (FIG. 5).

Conclusion: There is a recovery in the metabolic and lubricating saccharides.

Example 6

Example 6 shows the case of reactivation of somatic recognition and proves that this method is able to recognize tumoral and cancer cells allowing the expression of abnormal conditions providing the recognition mechanisms between the MHCII protein molecules and CD'8s so they could be eliminated via immunological routes. As in previous cases intermediate sugars participate as well in the identification. This example is displayed in the graph of FIG. 6 wherein the ordinates express the relative severity with cancelled surgery of prostate cancer with metastasis, (CPM) and in the abscissas the expected survival time (tx) without treatment, in the order of 5 weeks.

The horizontal dotted line, indicates what occurred after the treatment of this method and which exceeded one hundred weeks, prolonging survival by more than 20 times (20tx) and furthermore with an excellent health level allowing efficient work performance.

Example 7

A further example in this field is the case of a female adult with bone marrow cancer treated with two chemotherapies before starting treatment with this method. In FIG. 7, chemotherapies are marked in the ordinates as QT1 and QT2.

The time of survival without treatment is marked in the abscissas as tx and is in the order of two weeks without this method.

This case was treated on a daily basis with exposures of half an hour each.

The dotted line shows survival ten times longer (10tx) than that expected without the use of this method. The survival was with an excellent health level.

Example 8

Tables 1–3 show the results of patients with brain diseases treated according to the present invention. These patients were reported to be suffering from epilepsy, migraines, cerebral palsy, and related conditions. Of the 32 patients in this group, 4 had excellent responses, 25 had good responses, and 3 showed no change.

TABLE 1

RESPONSE REPORT-PATHOLOGY

| DATE | SEX | AGE | RESPONSE | PATHOLOGY |
|---|---|---|---|---|
| 11/20/93 | FEMALE | 10 | AAA-EXELL | AAO-EPILEPSY |
| 5/10/93 | MALE | 10 | AAA-EXELL | AAO-EPILEPSY |
| 04/16/94 | FEMALE | 46 | AAA-EXELL | AAO-MIGRAINES- |

TABLE 1-continued

RESPONSE REPORT-PATHOLOGY

| DATE | SEX | AGE | RESPONSE | PATHOLOGY |
|---|---|---|---|---|
| 03/20/94 | FEMALE | 51 | AAA-EXELL | KIDNEY AAO-EPILEPSY |

TABLE 3

RESPONSE REPOT-PATHOLOGY

| DATE | SEX | AGE | RESPONSE | PATHOLOGY |
|---|---|---|---|---|
| 05/25/94 | MALE | 32 | AAC-SAME | AAO-EPILEPSY |
| 07/18/94 | FEMALE | 1 | AAC-SAME | AAO-CEREBRAL-STROKE |
| 07/16/94 | FEMALE | 1 | AAC-SAME | AAO-HYDROCEPHALUS |

TABLE 2

RESPONSE REPORT-PATHOLOGY

| DATE | SEX | AGE | RESPONSE | PATHOLOGY |
|---|---|---|---|---|
| 09/23/91 | MALE | 20 | AAB-GOOD | AAO-EPILEPSY |
| 12/15/92 | FEMALE | 23 | AAB-GOOD | AAO-EPILEPSY |
| 10/06/93 | MALE | 1 | AAB-GOOD | AAO-CHILD EPILEPSY |
| 07/25/91 | MALE | 0 | AAB-GOOD | AAO-EPILEPSY |
| 11/01/91 | MALE | 18 | AAB-GOOD | AAO-BAD COORDINATION |
| 05/21/90 | MALE | 70 | AAB-GOOD | AAO-POOR CEREBRAL IRRIGATION |
| 10/13/93 | FEMALE | 13 | AAB-GOOD | AAO-CEREBRAL PARALYSIS |
| 01/22/94 | MALE | 9 | AAB-GOOD | AAO-CEREBRAL PARALYSIS |
| 01/26/94 | FEMALE | 8 | AAB-GOOD | AAO-CEREBRAL PARALYSIS |
| 01/26/94 | FEMALE | 4 | AAB-GOOD | AAO-CEREBRAL PARALYSIS |
| 01/26/94 | FEMALE | 22 | AAB-GOOD | AAO-HYPERKINETIC |
| 2/11/94 | FEMALE | 3 | AAB-GOOD | AAO-CEREBRAL PARALYSIS |
| 2/12/94 | MALE | 12 | AAB-GOOD | AAO-MENTAL RETARDED |
| 04/16/94 | MALE | 33 | AAB-GOOD | AAO-MEMORY LOSS |
| 05/21/94 | FEMALE | 2 | AAB-GOOD | AAO-CEREBRAL INJURY |
| 05/24/94 | FEMALE | 1 | AAB-GOOD | AAO-CEREBRAL INJURY |
| 6/07/94 | FEMALE | 35 | AAB-GOOD | AAO-EPILEPSY |
| 8/02/94 | FEMALE | 27 | AAB-GOOD | AAO-MIGRAIN, GASTRITIS |
| 09/23/94 | FEMALE | 40 | AAB-GOOD | AAO-MENTAL RETARDED |
| 2/01/95 | FEMALE | 20 | AAB-GOOD | AAO-DEPRESSION, RESTLESNESS |
| 4/07/95 | MALE | 25 | AAB-GOOD | AAO-PSYCOSYS, SCHIZOPHRENIA |
| 07/15/95 | FEMALE | 12 | AAB-GOOD | AAO-SLOW LEARNING |
| 07/19/95 | FEMALE | 9 | AAB-GOOD | AAO-EPILEPSY |
| 3/01/95 | FEMALE | 53 | AAB-GOOD | AAO-EPILEPSY |
| 4/05/96 | MALE | 11 | AAB-GOOD | AAO-HYDROCEPHALUS |

Example 9

Tables 4–5 show the results of patients with HIV treated according to the present invention. Of the 7 patients in this group, 1 had an excellent response, and 6 had good responses.

TABLE 4

RESPONSE REPORT-PATHOLOGY

| DATE | SEX | AGE | RESPONSE | PATHOLOGY |
|---|---|---|---|---|
| 08/23/93 | FEMALE | 38 | AAA-EXELL | AAV-H.I.V. |

TABLE 5

RESPONSE REPORT-PATHOLOGY

| DATE | SEX | AGE | RESPONSE | PATHOLOGY |
|---|---|---|---|---|
| 11/08/93 | MALE | 26 | AAB-GOOD | AAV-H.I.V. |
| 2/10/94 | MALE | 40 | AAB-GOOD | AAV-H.I.V. |
| 04/15/94 | MALE | 52 | AAB-GOOD | AAV-H.I.V. |
| 12/20/94 | MALE | 0 | AAB-GOOD | AAV-H.I.V. |
| 2/02/91 | FEMALE | 43 | AAB-GOOD | AAV-H.I.V. |
| 04/28/92 | MALE | 32 | AAB-GOOD | AAV-H.I.V. |

Examples 10

Tables 6–8 show the results of patients with cancer treated according to the present invention. These pateints were reported to be suffering from leukemia and various solid tumors. Of the 36 patients in this group, 6 had excellent responses, 27 had good responses, and 3 showed no change.

TABLE 6

RESPONSE REPORT-PATHOLOGY

| DATE | SEX | AGE | RESPONSE | PATHOLOGY |
|---|---|---|---|---|
| 8/01/91 | MALE | 60 | AAA-EXELL | AAC-CANCER |
| 11/28/89 | FEMALE | 51 | AAA-EXELL | AAC-CANCEROUS TUMOUR |
| 02/25/90 | MALE | 0 | AAA-EXELL | AAC-CANCER |
| 5/10/91 | MALE | 0 | AAA-EXELL | AAC-SPINAL CORD CANCER |
| 03/25/94 | MALE | 22 | AAA-EXELL | AAC-TESTICLE CANCER |
| 11/21/94 | FEMALE | 17 | AAA-EXELL | AAC-LEUKAEMIA |

TABLE 8

RESPONSE REPORT-PATHOLOGY

| DATE | SEX | AGE | RESPONSE | PATHOLOGY |
|---|---|---|---|---|
| 04/15/91 | MALE | 55 | AAC-SAME | AAC-SKIN CANCER |
| 6/03/95 | FEMALE | 3 | AAC-SAME | AAC-LEUKAEMIA |
| 09/22/95 | FEMALE | 44 | AAC-SAME | AAC-CANCER |

TABLE 7

RESPONSE REPORT-PATHOLOGY

| DATE | SEX | AGE | RESPONSE | PATHOLOGY |
|---|---|---|---|---|
| 08/25/93 | FEMALE | 29 | AAB-GOOD | AAC-CANCER |
| 02/25/93 | FEMALE | 42 | AAB-GOOD | AAC-CANCER |
| 09/14/92 | FEMALE | 83 | AAB-GOOD | AAC-CANCEROUS TUMOUR |
| 01/22/94 | FEMALE | 55 | AAB-GOOD | AAC-CANCER |
| 8/04/94 | MALE | 75 | AAB-GOOD | AAC-CANCER |
| 08/26/94 | MALE | 60 | AAB-GOOD | AAC-GALL-BLADDER CANCER |
| 07/14/94 | FEMALE | 77 | AAB-GOOD | AAC-BREAST CANCER |

TABLE 7-continued

RESPONSE REPORT-PATHOLOGY

| DATE | SEX | AGE | RESPONSE | PATHOLOGY |
|---|---|---|---|---|
| 7/08/94 | MALE | 51 | AAB-GOOD | AAC-TUMOUR |
| 8/08/94 | MALE | 75 | AAB-GOOD | AAC-PROSTATE CANCER |
| 10/08/94 | FEMALE | 56 | AAB-GOOD | AAC-CANCEROUS TUMOR |
| 11/03/94 | FEMALE | 82 | AAB-GOOD | AAC-CANCER |
| 11/03/94 | FEMALE | 64 | AAB-GOOD | AAC-CANCER |
| 11/16/94 | FEMALE | 61 | AAB-GOOD | AAC-CANCEROUS TUMOR |
| 11/30/94 | FEMALE | 52 | AAB-GOOD | AAC-CANCER |
| 01/23/95 | FEMALE | 58 | AAB-GOOD | AAC-CANCER |
| 2/02/95 | MALE | 17 | AAB-GOOD | AAC-CANCER |
| 02/21/95 | FEMALE | 52 | AAB-GOOD | AAC-CANCER |
| 4/07/95 | FEMALE | 32 | AAB-GOOD | AAC-CANCER |
| 4/08/95 | MALE | 18 | AAB-GOOD | AAC-NEUROBLASTEM |
| 4/11/94 | FEMALE | 39 | AAB-GOOD | AAC-CANCER |
| 5/05/95 | MALE | 75 | AAB-GOOD | AAC-CANCER |
| 05/13/95 | FEMALE | 40 | AAB-GOOD | AAC-CANCER |
| 05/26/95 | FEMALE | 11 | AAB-GOOD | AAC-CEREBRAL TUMOUR |
| 05/26/95 | FEMALE | 53 | AAB-GOOD | AAC-CANCER |
| 8/05/95 | MALE | 36 | AAB-GOOD | AAC-CANCER |
| 8/11/95 | FEMALE | 54 | AAB-GOOD | AAC-CANCER |
| 08/23/95 | FEMALE | 51 | AAB-GOOD | AAC-CANCER |

Example 11

Tables 9 and 10 show the results of patients with diabetes treated according to the present invention. Of the 9 patients in the group, 0 had excellent response, 8 had good responses, and 1 showed no change.

TABLE 9

RESPONSE REPORT-PATHOLOGY

| DATE | SEX | AGE | RESPONSE | PATHOLOGY |
|---|---|---|---|---|
| 4/01/91 | MALE | 16 | AAB-GOOD | AAE-DIABETES |
| 01/19/94 | FEMALE | 24 | AAB-GOOD | AAE-DIABETES |
| 05/21/94 | MALE | 75 | AAB-GOOD | AAE-DIABETES MIELLITUS |
| 02/28/95 | MALE | 46 | AAB-GOOD | AAE-DIABETES |
| 03/14/95 | FEMALE | 41 | AAB-GOOD | AAE-DIABETES |
| 03/15/95 | FEMALE | 20 | AAB-GOOD | AAE-DIABETES |
| 04/22/95 | FEMALE | 43 | AAB-GOOD | AAE-DIABETES |
| 4/07/96 | MALE | 73 | AAB-GOOD | AAE-DIABETES |

TABLE 10

RESPONSE REPORT-PATHOLOGY

| DATE | SEX | AGE | RESPONSE | PATHOLOGY |
|---|---|---|---|---|
| 04/15/93 | FEMALE | 54 | AAC-SAME | AAE-DIABETIS |

We claim:

1. A process for altering the three dimensional structure of saccharides to reactivate pattern recognition mechanisms between antigens and antibodies, in a patient in need of such reactivation, comprising the following steps:
   specifically diagnosing a patient's condition;
   correlating infection mechanisms with recognition immunologic defense mechanisms,
   selecting an appropriate wavelength for treatment; and
   exposing the patient and thus the patient's saccharides to electromagnetic energy in the range of 100–1000 Gauss using a sequence of negative or positive phases, wherein said electromagnetic energy is simultaneously combined with photonic energy at a wavelength in the range of 3000 to 7000 Å resulting in an alteration of the three dimensional structure of said saccharides.

2. The process according to claim 1, wherein the electromagnetic energy is in the range of 300–600 Gauss.

3. The process according to claim 1, wherein the frequency of the electromagnetic energy varies between 5 Hz and 50 kHz.

4. The process according to claim 3, wherein the frequency of the electromagnetic energy varies between 50 Hz and 5 kHz.

5. The process according to claim 1, wherein the wavelength of the photonic energy varies between 4000 and 6000 Å.

6. The process according to claim 1, wherein the frequency of the photonic energy varies in the range of 400 to 800 terahertz.

7. The process according to claim 6, wherein the frequency of the photonic energy varies in the range of 500 and 660 terahertz.

8. The process according to claim 1, wherein the electromagnetic energy in terahertz frequencies varies in the range from 1.5 electron volts to 3.5 electron volts, polarized or non-polarized and with 3 to 3000 kilocalories per mole of photons availability.

9. The process according to claim 8, wherein said energy varies within the range of 2 to 2.8 electron volts.

10. The process according to claim 8, wherein the electromagnetic energy varies in the range of 3 to 300 kilocalories per mole of photons available.

11. The process according to claim 1, wherein said patient is exposed to one source of energy or to two different sources of energy, wherein when the patient is exposed to two different sources of energy, the two sources are in Gauss/Hertz or electron-volts/terahertz, and wherein the energy sources are independently constant or pulsating.

12. The process according to claim 11, wherein the exposure of the patient to the energy is carried out in a range of one exposure per day to one exposure per month, with exposure time varying from 5 minutes to 50 minutes each time.

13. The process according to claim 12, wherein the exposure regimen is one 50 minute exposure per day.

14. The process according to claim 12, wherein the exposure regimen is an exposure each third day for a time of 45 minutes per exposure.

15. The process according to claim 12, wherein the exposure regimen is two times a day, for 30 minutes each exposure.

16. The process according to claim 11, wherein the blood pH of the patient during the exposure is from 3 to 8.

17. The process according to claim 16, wherein the blood pH of the patient during exposure is from 7.3 to 7.6.

18. A process for altering the three dimensional structure of saccharides, to reactivate pattern recognition mechanisms between antigens and antibodies comprising:
   correlating infection mechanisms with recognition immunologic defense mechanisms,
   selecting an appropriate wavelength for treatment, and
   exposing saccharides to electromagnetic energy in the range of 100–1000 Gauss using a sequence of negative and positive phases, simultaneously combined with photonic energy with a wavelength in the range of 3000 to 7000 Å.

19. A process for the treatment of an HIV infection in a patient in need of such treatment, comprising:

correlating infection mechanisms with recognition immunologic defense mechanisms, selecting an appropriate wavelength for treatment; and exposing a patient with an HIV infection to electromagnetic energy in the range of 100–1000 Gauss using a sequence of negative and positive phases, simultaneously combined with photonic energy with a wavelength in the range of 3000 to 7000 Å.

20. The process of claim 19, wherein the electromagnetic energy is in the range of 300–600 Gauss.

* * * * *